United States Patent [19]

Brown et al.

[11] Patent Number: 5,094,343
[45] Date of Patent: Mar. 10, 1992

[54] COMBINATION BEVERAGE TRAY AND SUN VISOR

[76] Inventors: Harry Brown, 876 Peninsula; Andrew Primack, 2426 Michigan Dr., both of Claremont, Calif. 91711

[21] Appl. No.: 492,630

[22] Filed: Mar. 13, 1990

[51] Int. Cl.$^5$ .............................. A42B 1/20; A42B 1/22
[52] U.S. Cl. ................................. 206/216; 206/564; 229/103; 229/904; 2/196; 2/177
[58] Field of Search ............... 2/184.5, 209.3, 171, 2/183, 209.1, 196, 177; 40/329; 229/904, 103; 206/232, 216, 427, 564, 607

[56] References Cited

U.S. PATENT DOCUMENTS

| | | | |
|---|---|---|---|
| 1,418,198 | 5/1922 | Neppell | 2/183 X |
| 2,083,000 | 6/1937 | Bennard | 2/196 |
| 2,203,028 | 6/1940 | Parrillo | 40/329 X |
| 2,771,232 | 11/1956 | Reed | 229/904 X |
| 2,924,372 | 2/1960 | Kirkelay | 229/904 X |
| 3,915,371 | 10/1975 | Crabtree | 229/904 X |
| 4,192,017 | 3/1980 | Fay | 40/329 X |
| 4,246,659 | 1/1981 | Lyons | 2/209.3 X |
| 4,364,123 | 12/1982 | Sam | 2/209.1 |
| 4,477,014 | 10/1984 | Brandenburger | 206/607 X |
| 4,719,651 | 1/1988 | Tereshinski | 2/209.1 X |
| 4,837,865 | 6/1989 | Roth | 2/177 X |

Primary Examiner—Paul T. Sewell
Assistant Examiner—Jacob K. Ackun, Jr.
Attorney, Agent, or Firm—Fulwider, Patton, Lee & Utecht

[57] ABSTRACT

A combination beverage tray and sun visor comprised of a beverage tray having raised side walls and including a pre-formed perforation along a portion of the junction of the base of said tray and the side walls wherein the base may be separated from the sidewalls thereby forming an opening which allows the beverage tray to be converted into a sun visor and worn upon one's head.

11 Claims, 1 Drawing Sheet

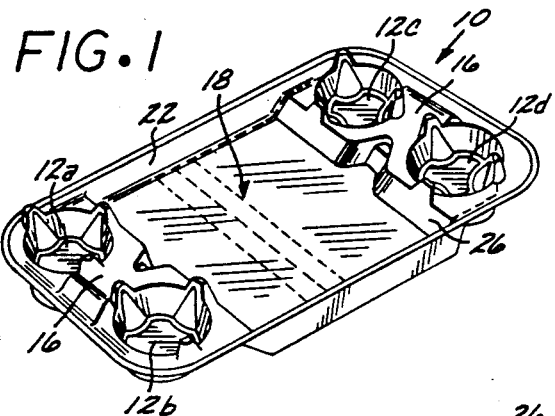
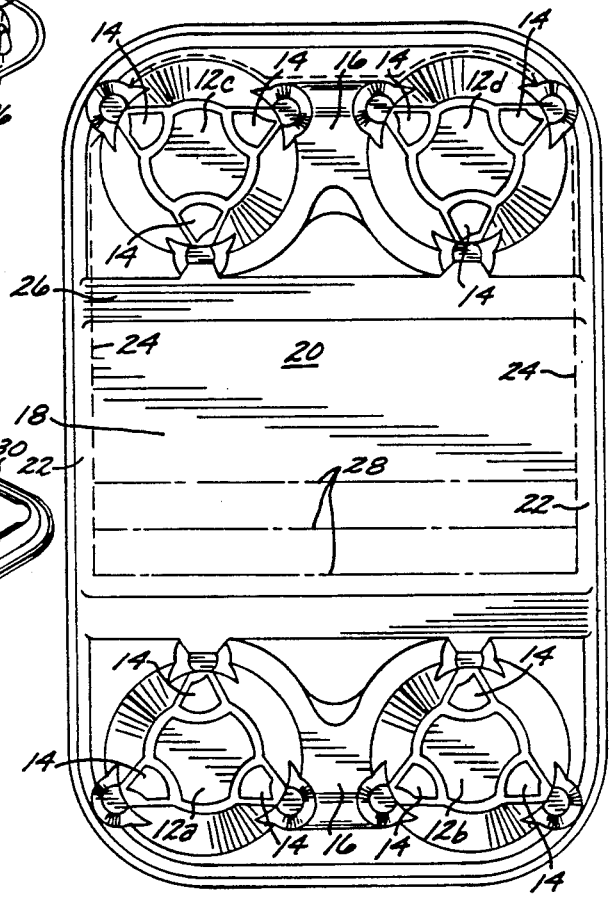
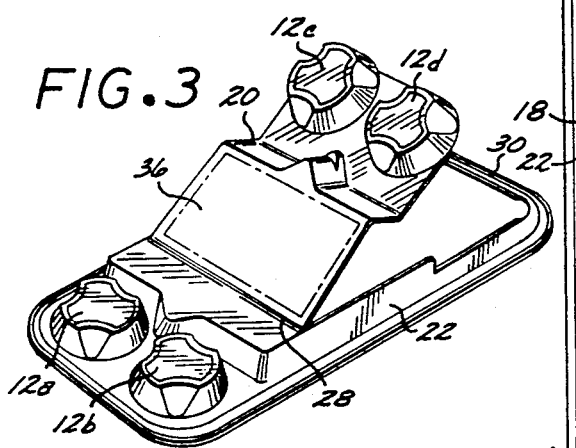
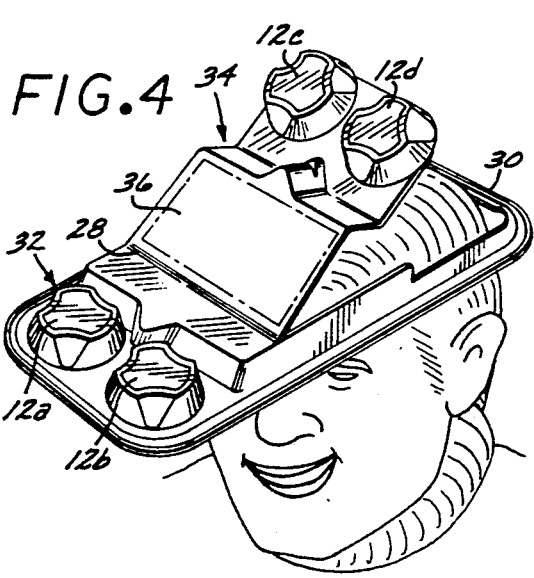
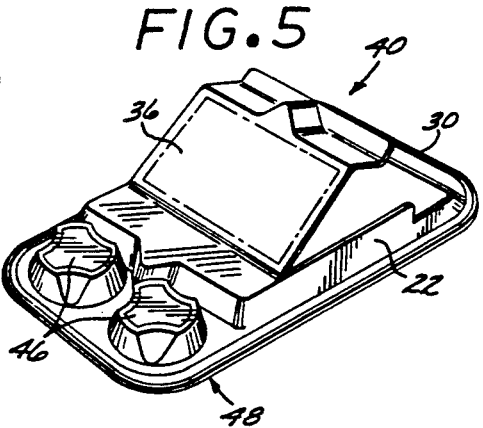

COMBINATION BEVERAGE TRAY AND SUN VISOR

FIELD OF INVENTION

This invention relates to the field of hats or sun visors. More particularly, the invention relates to the field of novelty items wherein an item designed and constructed for use as a beverage and/or food tray may subsequently may be converted to use as a sun visor or hat.

BACKGROUND OF INVENTION

It has long been known to utilize hats, sun visors or other forms of head coverings to shield one's head and/or eyes from the sun. The need for a head covering of one form or another has been particularly acute at outdoor sporting events such as baseball or football games wherein the spectators are frequently exposed to the direct sunlight for extended periods of times. All to often the spectator has forgotten his or her hat or visor and is forced to purchase a hat or visor at the sporting event, frequently at decidedly marked up prices, in order to avoid suffering from over exposure to the sun resulting in either sunburn or in more extreme cases, sun stroke.

It is also been previously known to utilize pre-formed or easily expandable food and beverage trays at sporting events for the transportation of the spectator's food and beverage purchases from the concession stands to the spectator's seating area. Prior devices are frequently constructed from an inexpensive cardboard or paper mulch mixture. Normally these beverage trays have been discarded and thrown upon the stadium floors by the spectator upon his or her return to their seating area.

A need therefore exists for a method of improvising or otherwise constructing a hat or sun visor to protect spectators at sporting events when exposed to the direct sun light while at the same time helping to eliminate the indiscriminate discarding of waste material such as food and beverage trays.

It is an object of this invention to provide a food or beverage tray which upon completion of the transportation function as a food or beverage tray for transporting food and or beverages from the concession stand to the spectator's seating area, can be transformed into a hat or sun visor.

It is also an object of this invention to provide a food or beverage tray which upon being converted to a sun visor can be utilized as an advertising medium or novelty item.

SUMMARY OF INVENTION

The present invention is comprised of a conventional food or beverage tray of the type traditionally utilized at sporting events, concerts, etc. The tray is constructed out of lightweight material such as cardboard, paper pulp or other lightweight, inexpensive material. In the present invention the beverage tray also includes a perforated outline along the junction of the bottom and side walls of the container such that upon completion of the use of the beverage tray as a tray, the individual may separate the bottom of the beverage tray from the side walls along the pre-formed perforation outline and fold the bottom of the tray away from the main body of the tray. The folding of the tray bottom away from the side walls creates an opening which allows the tray to be placed on the users head as a hat or sun visor. In order to allow users of differing head sizes to convert the beverage tray into a hat or visor a plurality of crease lines are pre-formed across the bottom of the beverage tray so that the user may readily fold the bottom along the appropriate crease so as to create an opening approximately the hat size of the individual.

The present invention is also intended to be utilized as a novelty or advertising item wherein a rectangular area is provided on the underside portion of the bottom of the container for the display of advertising slogans and/or logos. Upon the tray being converted to a hat or sun visor, the advertising or logo imprinted upon the underside of the bottom of the beverage tray stands or is slanted in an upright position so as to be visible to anyone facing the individual wearing the visor.

DETAILED DESCRIPTION OF DRAWINGS

FIG. 1 is a perspective view of a first embodiment of the subject invention.

FIG. 2 is a top view of the embodiment shown in FIG. 1.

FIG. 3 is a perspective view of the embodiment shown in FIG. 1 when converted to the hat or sun visor mode.

FIG. 4 is a perspective view of the first embodiment of the subject invention worn in place on an individual's head.

FIG. 5 is a perspective view of an alternate embodiment of the subject invention.

DETAILED DESCRIPTION

A preferred embodiment the subject invention is illustrated in FIGS. 1 through 4. As shown in FIG. 1, the combination food/beverage tray and sun visor of the instance invention is comprised of a pre-formed beverage tray 10. The beverage tray 10 itself is of the type known in the art. The tray 10 is preferably of a rectangular configuration having pre-formed receptacles 12, a, b, c, d for holding up to four beverage cups. As illustrated in FIG. 1, a pair of beverage receptacles 12 is located at each end of the tray 10. The beverage receptacles 12 are of a circular recessed configuration having a plurality of flexible, inwardly projecting support ribs 14 spaced equi-distance about the interior of the receptacle 12. The spacing of the support ribs 14 is designed to form a cup or container receiving area slightly smaller than the outside diameter of the actual beverage containers. The beverage container (not shown) is retained in place within the beverage receptacle 12 by press fitting the beverage container down into the receptacle 12 causing the flexible, inwardly protruding support ribs 14 to deflect outward to accommodate the beverage container which results in the ribs 14 exerting a griping or holding force on the beverage container so as to securely retain the beverage container within the beverage receptacle 12.

In the traditional beverage/food tray combination as shown in FIG. 1 the tray includes a raised platform or section 16 at opposing ends of the tray 10 with the beverage receptacles 12 being recessed within the raised platforms 16. A recessed center food storage section 18 is formed between the two raised platforms 16 for the storage and transportation of food items.

As shown in FIG. 2, a portion of the junction of the center section 18 of the beverage tray 10 and the side walls 22 is constructed with a pre-formed perforation outline 24 so as to facilitate the separation of a portion of the center section 18 from the side wall 22 of the tray 10. As illustrated in FIG. 2, the pre-formed perforation outline 24 commences at an intermediate point along the center section 18 of the tray 10 and extends rearward along the junction of the center section 18 and side wall 22 on each side of the beverage tray 10 and extends upward along the junction of shoulder 26 and sidewall 22 and continues around the junction of raised platform 16 and side walls 22. Shoulder 26 connects center section 18 and raised platform 16. The portion of the container outlined by the pre-formed perforation 24 is referred to as the floor 20. In order to convert the beverage tray 10 from the tray mode to the sun visor mode the user simply applies force to the floor 20 of the tray 10 causing the floor 20 of the tray 10 to separate from the side walls 22 along the perforation lines 24. The invention in its separated sun visor state is shown in FIG. 3.

As illustrated in FIG. 2, pre-set or pre-formed folding or crease lines 28 are formed widthwise across the floor 20 of the tray 10 to facilitate the folding of the floor 20 of the tray 10 away from the main body of the tray 10. The user can adjust the sun visor to fit the size of his or her head, as shown in FIG. 4, by simply folding the floor portion 20 of the tray 10 away from the main body of the tray 10 along the performed fold or crease 28 line which corresponds to that individual's hat size. When the floor 20 is folded away from the main body the side walls 22 form a hat band 30 as shown in FIG. 3.

Therefore, in order to convert the beverage tray 10 to a sun visor for utilization as illustrated in FIG. 4, the user simply separates the floor section 20 of the container from the side walls 22 by exerting a force along the perforation line 24 which will result in the floor 20 separating from the side walls 22. The user then folds the floor 20 away from the main body as illustrated in FIG. 3 along the preformed fold line 28 which will result in the visor having an opening sufficient to accommodate the user's head. To utilize the beverage tray 10 as a sun visor at this point it may simply be placed on the user's head as shown in FIG. 4. The tray 10 is retained on the users head by means of hat band 30 formed by the now separated portion of side wall 22.

As shown in FIG. 4, a hat or sun visor has been formed in which the brim or visor section 32 is formed by the from raised platform section 16 of the tray 10. The floor section 20, now separated from the sidewall 22, forms the crown 34 of the hat and the remaining side wall section 22 services as the hat band 30 holding the invention in place on the user's head.

As discussed earlier, the present invention is also intended to be used as an advertizing or novelty device wherein advertising logos or novelty sayings or drawings, etc. may be placed upon the bottom of the container such that when the container is converted to a visor, the logo is moved into a highly visible position. As shown in FIG. 3, this advertising or logo section 36 is formed by the underside of the portion of the floor 20 formed by the underside of center section 18 of the tray which is folded upward. This advertising or logo section 36 is shown in FIGS. 3, 4 and 5.

In an alternate embodiment of the invention, a two cup beverage and food tray 40 is utilized as shown in FIG. 5. In this embodiment the portion of the floor 30 of the tray 40 which is folded upward is the rearward portion of the tray 40 without the beverage receptacles 46. The forward section of the tray 40 with the two recessed beverage receptacles 46 forms the brim visor portion 48 of the hat. The construction of the tray 40 is otherwise the same as discussed in connection with the first embodiment illustrated in FIGS. 1-4 and will not be repeated.

Having described our invention in detail, it is to be understood that other embodiments or equivalents of the invention described herein may be apparent to those skilled in the art. The invention is not intended to be limited to the embodiments described herein but is to be accorded the full breath and scope of the claims appended hereto.

What is claimed:

1. A combination food and beverage carrying tray and sun visor convertible from a carrying tray into a sun visor comprising:
    a tray, said tray having a base with said base having two pairs of parallel side edges and raised sidewalls connected to and extending perpendicular to each of said parallel side edges and extending about the periphery of said base;
    a plurality of beverage container receptacles integrally formed within said tray;
    a perforated separation line beginning at a first intermediate point along the junction between one of said base side edges and sidewalls and extending along the junction of the base and raised sidewalls, to a second intermediate point along the junction of the base and opposing sidewall opposite the beginning point; and
    at least one pre-formed fold line extending across said base, the first of said at least one pre-formed fold line connecting the starting and end points of the perforated separation line.

2. The combination food and beverage carrying tray and sun visor of claim 1 wherein said beverage container receptacles are integrally formed within the base of said tray.

3. The combination food and beverage carrying tray and sun visor of claim 1 wherein the base of said tray includes a raised section at one end of said base and said beverage container receptacles are integrally formed within said raised section.

4. The combination food and beverage carrying tray and sun visor of claim 1 wherein the base of said tray includes a raised section at each end of said base and said beverage container receptacles are integrally formed within said raised sections.

5. The combination food and beverage carrying tray and sun visor of claim 1 wherein display means for visually displaying lettering or graphics, either individually or in combination are provided on the underside of said base.

6. The combination food and beverage carrying tray and sun visor of claim 1 wherein there are a plurality of pre-formed fold lines for forming sun visors of varying head sizes.

7. A combination food and beverage carrying tray and sun visor convertible from a carrying tray into a sun visor comprising:
    a tray, said tray having a recessed base and at least one raised end section connected to said base, and raised sidewalls connected to and extending perpendicularly from said base and raised end section and extending about the periphery of said base and raised end section;
    a plurality of beverage container receptacles integrally formed in each of said at least one raised end section;

a perforated separation line extending along the junction of the base and raised sidewalls and raised section and sidewalls, said perforated separation line commencing at a first intermediate point along the junction of the base and sidewall and continuing along said junction to a second intermediate point opposite it along the junction of the base and opposing sidewall; and at least one pre-formed fold line extending across said base, said first of said at least one of pre-formed fold line connecting to the starting and end points of the perforated separation line.

8. The combination food and beverage carrying tray and sun visor of claim 7 including display means for visually displaying letters or graphics, either individually or in combination provided on the underside of said base.

9. The combination food and beverage carrying tray and sun visor of claim 7 wherein there are a plurality of pre-formed fold lines for forming sun visors of varying head sizes.

10. A combination food and beverage carrying tray and sun visor convertible from a tray into a sun visor comprising:

a tray, said tray having a base and raised sidewalls connected to and extending perpendicularly from said base, said sidewalls extending continuously around the periphery of said base;

a pre-weakened separation line extending partially along the junction of the base and sidewalls, said separation line commencing at a first intermediate point along said junction and continuing along said junction to a second intermediate point opposite said first intermediate point;

at least one preformed fold line extending across said base and connecting said first and second intermediate points; and a plurality of beverage container receptacles integrally formed within said tray wherein the base of said tray includes a raised section at one end of said base and said beverage container receptacles are integrally formed within said raised section.

11. A food and beverage carrying tray and sun visor convertible from a tray into a sun visor comprising:

a tray, said tray having a base and raised sidewalls connected to and extending perpendicularly from said base, said sidewalls extending continuously around the periphery of said base;

a pre-weakened separation line extending partially along the junction of the base and sidewalls, said separation line commencing at a first intermediate point along said junction and continuing along said junction to a second intermediate point opposite said first intermediate point;

at least one preformed fold line extending across said base and connecting said first and second intermediate points; and a plurality of beverage container receptacles integrally formed within said tray wherein the base of said tray includes a raised section at each end of said base and said beverage container receptacles are integrally formed within said raised sections.

* * * * *